United States Patent [19]

Weber et al.

[11] 3,932,658

[45] Jan. 13, 1976

[54] COMPOSITION AND METHOD FOR LOWER BLOOD SUGAR CONTAINING N-[4-(β-<2-METHOXY-5-CHLORO-BENZAMIDO>-ETHYL)-BENZENESULFONYL]-N'-CYCLOPENTYL-UREA

[75] Inventors: Helmut Weber, Frankfurt am Main; Walter Aumuller; Karl Muth, both of Kelkheim-Taunus; Rudi Weyer, Frankfurt am Main, all of Germany

[73] Assignee: Hoechst Aktiengesellschaft, Frankfurt, Germany

[22] Filed: Oct. 16, 1972

[21] Appl. No.: 297,679

Related U.S. Application Data

[62] Division of Ser. No. 10,659, Feb. 11, 1970, Pat. No. 3,754,030.

[52] U.S. Cl. ............................ 424/321; 260/553 D
[51] Int. Cl. ..................................... A61k 27/00
[58] Field of Search ............................ 424/321

[56] References Cited
UNITED STATES PATENTS

3,183,260   5/1965   Loez ............................... 260/553 D
3,406,199   10/1968  Weber et al. ................. 260/553 DA
3,426,067   2/1969   Weber et al. ................. 260/553 DA
3,449,346   6/1969   Anmuller et al. ............ 260/553 DA

OTHER PUBLICATIONS

Dervent Belgium Patent Report, 5/67, Sec. 3, p. 1, 1967.

*Primary Examiner*—Erome D. Goldberg
*Attorney, Agent, or Firm*—Curtis, Morris & Safford

[57] ABSTRACT

N-[4-(β-<2-methoxy-5-chloro-benzamido>-ethyl)-benzenesulfonyl]-N'-cyclopentyl-urea of the formula

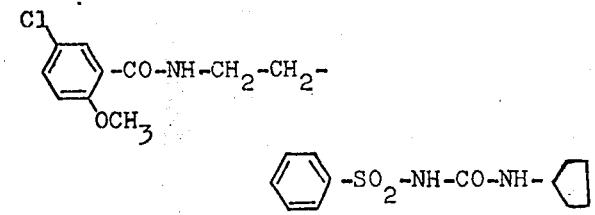

having a long-lasting and strong hypoglycemic action in the treatment of diabetes mellitus and a process for its manufacture.

2 Claims, No Drawings

3,932,658

COMPOSITION AND METHOD FOR LOWER BLOOD SUGAR CONTAINING N-[4-(>-<2-METHOXY-5-CHLORO-BENZAMIDO>-ETHYL)-BENZENESULFONYL]-N'-CYCLOPENTYL-UREA

This is a division of application Ser. No. 10,659 filed Feb. 11, 1970, now Pat. No. 3,754,030.

The present invention relates to N-[4-($\beta$-<2-methoxy-5-chloro-benzamido>-ethyl)-benzenesulfonyl]-N'-cyclopentylurea of the formula

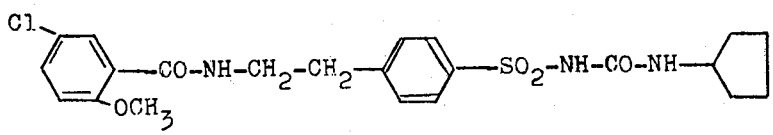

which in the free form or in the form of its salts has blood sugar lowering properties and is distinguished by a strong and long-lasting hypoglycemic action.

The present invention furthermore relates to processes for preparing this benzenesulfonyl-urea, wherein a. a benzensulfonyl-isocyanate, a benzenesulfonyl-carbamic acid ester, a benzenesulfonyl-thiolcarbamic acid ester, a benzenesulfonyl-urea, a benzenesulfonyl-semicarbazide or a benzenesulfonyl-semicarbazone which is substituted in para-position by the group

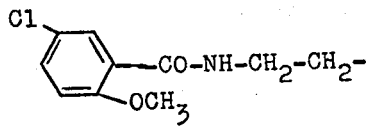

is reacted with cyclopentyl-amine or a salt thereof, or 4-($\beta$-<2-methoxy-5-chloro-benzamido>-ethyl)-benzenesulfonamide of the formula

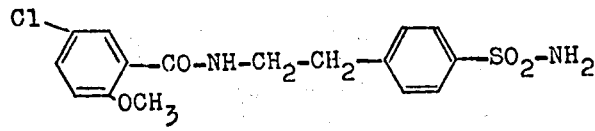

or a salt thereof is reacted with a cyclopentyl-isocyanate, carbamic acid ester, thiolcarbamic acid ester, carbamic acid halide or urea, b. a correspondingly substituted benzenesulfonyl-isourea ether, benzenesulfonyl-isothiourea ether, benzenesulfonylisourea ester, benzenesulfonyl-parabanic acid or benzenesulfonyl-haloformic acid amidine is hydrolized, or a compound of the formula

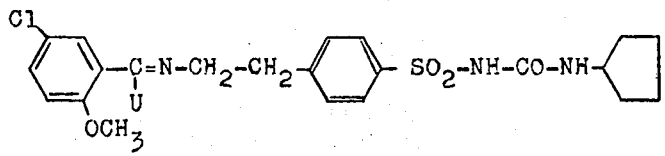

or a parabanic acid derivative thereof or a compound of the formula

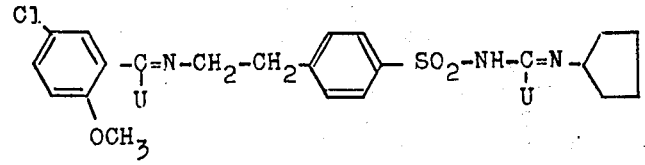

wherein U stands for oxygen-lower-alkyl, sulfur-lower-alkyl or halogen (preferably chlorine), is saponified or water is added in a correspondingly substituted carbodiimide, c. in a correspondingly substituted benzenesulfonyl-thioures or thiobenzamido-alkyl-benzene-sulfonyl-urea, the sulfur atom is replaced by an oxygen atom;

d. a correspondingly substituted benzenesulfinyl-urea or benzene-sulfenyl-urea is oxidized, e. the group

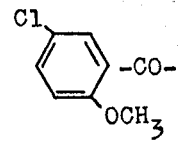

is introduced by acylation in one or more steps into N-[4-($\beta$-aminoethyl)-benzenesulfonyl]-N'-cyclopentyl-urea of the formula

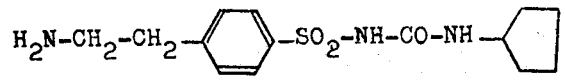

or f. a correspondingly substituted benzenesulfonyl halide is reacted with cyclopentyl-urea or an alkali metal salt thereof or a correspondingly substituted benzenesulfinic acid halide or, in the presence of an acid condensation agent, even a correspondingly substituted benzenesulfinic acid or an alkali metal salt thereof is reacted with N-cyclopentyl-N'-hydroxy-urea, and, if desired, the reaction product obtained is treated with an alkaline agent for salt formation.

The aforesaid benzenesulfonyl-carbamic acid esters or benzene-sulfonyl-thiolcarbamic acid esters may contain in the alcoholic component an alkyl group or an aryl group or even a heterocyclic radical. Since this radical is split off during the reaction, its chemical constitution has no influence on the nature of the final product and may, therefore, be varied within wide limits. The same applies to the cyclopentyl-amine-substituted carbamic acid esters and the corresponding thiolcarbamic acid esters.

As carbamic acid halide, the chloride is preferably used. The benzenesulfonyl-ureas used as starting materials in the process of the present invention may be unsubstituted at the side of the urea molecule opposite to the sulfonyl group or may be mono- or, especially, di-substituted. Since these substituents are split off during the reaction with the amines, their nature can be varied within wide limits. In addition to benzenesulfonyl-ureas which carry alkyl, aryl, acyl or heterocyclic substituents, there may also be used benzenesulfonyl-carbamoyl-imidazoles and similar compounds or bis-(benzenesulfonyl)-ureas which may carry at one of the nitrogen atoms a further substituent, for example a methyl group. For example, such bis-(benzene-sulfonyl)-ureas or also N-benzene-sulfonyl-N'-acyl-ureas may be treated with cyclopentylamine and the salts obtained may be heated to elevated temperatures, especially to a temperature above 100°C.

Furthermore, it is possible to start from cyclopentyl-urea or from a cyclopentyl-urea which is mono- or, especially, disubstituted at the free nitrogen atom, and to react it with

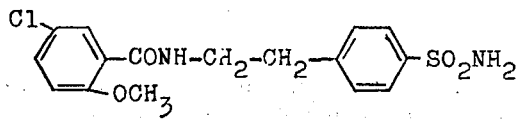

As such starting materials, there may be used for example N-cyclopentyl-urea, the corresponding N'-acetyl, N'-nitro, N'-cyclopentyl, N',N'-diphenyl- (in which case the two phenyl radicals may also be substituted or be linked with each other either directly or also by means of a bridge member such, for example, as —CH$_2$—, —NH—, —O— or —S—), N'-methyl-N'-phenyl, N',N'-dicyclohexyl-ureas as well as cyclopentyl-carbamoyl-imidazoles, -pyrazoles or -triazoles.

The hydrolysis of the benzenesulfonyl-parabanic acids, benzenesulfonyl-isourea ethers, benzenesulfonyl-isothiourea ethers, benzenesulfonyl-isourea esters or benzenesulfonylhaloformic acid amidines mentioned as starting substances is suitably carried out in an alkaline medium. Isourea ethers and isourea esters may also be hydrolized successfully in an acid medium.

The replacement of the sulfur atom in the correspondingly substituted benzenesulfonyl-thioureas by an oxygen atom can be effected in known manner, for example, with the aid of oxides or salts of heavy metals or with the use of oxidizing agents such, for example, as hydrogen peroxide, sodium peroxide, nitrous acid or permanganates.

The thioureas may also be desulfurized by treatment with phosgene or phosphorus pentachloride. The chloroformic acid amidines or chloroformic acid carbodiimides obtained as intermediates may be converted into the benzenesulfonyl-ureas by suitable measures such, for example, as by saponification or addition of water.

The acylation of the N-[4-(β-aminoethyl)-benzenesulfonyl]-N-cyclopentyl-urea may be carried out either in one step, for example by the reaction of correspondingly substituted benzoic acid halides, or it may be effected in several steps. As an example of the numerous possibilities of a stepwise acylation, there may be mentioned the reaction of aminoethyl-benzenesulfonyl-ureas with 2-methoxy-benzoyl chloride and the subsequent introduction of a chlorine atom into the benzene nucleus of the benzamido group.

The oxidation of the benzenesulfinyl-ureas or benzenesulfenyl-ureas may be carried out with the aid of known oxidizing agents, for example potassium permanganate.

As regards the reaction conditions, the methods of carrying out the process of the invention may, in general, be varied within wide limits and may be adapted to each individual case. For example, the reactions may be carried out in the presence or in the aabsence of solvents, at room temperature or at an elevated temperature.

Depending on the nature of the starting substances, one or other of the aforesaid methods may, in some cases, provide a desired individual benzenesulfonyl-urea only in a small yield or may be inappropriate for its synthesis. In such comparatively rare cases, the expert will have no difficulty in synthesizing the desired product according to one of the other methods of the process described.

The starting materials are prepared by methods that are generally known. For example, substituted benzenesulfonamides used as starting substances may be obtained by the reaction of the corresponding benzene compounds with chlorosulfonic acid and subsequently with ammonia or by acylation of p-aminoethyl-benzenesulfonamide with corresponding acid chlorides. The benzenesulfonyl-urethanes or benzenesulfonyl-ureas used as starting materials may be prepared, for example, from the corresponding benzenesulfonamides and haloformic acid alkyl esters or potassium cyanate (KOCN). Benzenesulfinyl-ureas or benzenesulfenyl-ureas may be obtained by the condensation of the corresponding sulfinyl chlorides or sulfenyl chlorides with ureas.

The hypoglycemic action of the afore-described benzenesulfonyl-urea can be ascertained by administering it in the form of the sodium salt in a dose of 10 mg/kg of body weight to normally fed rabbits and determining the blood sugar level according to the known method of Hagedorn-jensen or by means of an auto-analyzer for a prolonged period of time.

Thus, it has been found that N-[4-(β-<2-methoxy-5-chlorobenzamido>-ethyl)-benzenesulfonyl]-N'-cyclopentyl-urea (1) causes the lowering of the blood sugar level as indicated in the following Table.

For comparison, the lowering of the blood sugar level produced by the known N-[4-(β-<2-methoxy-5-chlorobenzamido>-ethyl)-benzenesulfonyl]-N'-cyclohexyl-urea (II) is also indicated in this Table.

Table

Lowering of the blood sugar level in rabbits, in per cents after oral administration 10 mg/kg

|  | after | | | | | hours | | |
| --- | --- | --- | --- | --- | --- | --- | --- | --- |
|  | 1 | 3 | 6 | 24 | 48 | 72 | 96 | 120 |
| Compound I | 18 | 39 | 36 | 45 | 50 | 41 | 27 | 0 |
| Compound II | — | 19 | — | 23 | 28 | 13 | 0 | — |

The benzenesulfonyl-urea of the present invention is preferably used for the manufacture of pharmaceutical preparations suitable for oral administration and for the lowering of the blood sugar level in the treatment of diabetes mellitus, for which purpose it may be used as such or in the form of its physiologically tolerable salts or in the presence of substances which cause salt formation. For the formation of salts, there may be used, for example, alkaline agents such as alkali metal- or alkaline earth metal hydroxides, carbonates or bicarbonates these are commonly used in the pharmaceutical industry to form physiologically tolerable salts.

The present invention therefore also provides pharmaceutical preparations that have hypoglycemic action and are suitable for oral administration in the treatment of diabetes mellitus, which preparations have preferably the form of tablets and contain as the active ingredient the benzenesulfonyl-urea of the invention or a salt thereof in admixture or conjunction with pharmaceutically suitable carriers such as talc, starch, lactose, tragacanth or magnesium stearate.

Such a pharmaceutical preparation, for example a tablet or a powder, containinng the benzenesulfonyl-ureaa of the invention or a physiologically tolerable salt thereof as the active substance, with or without one or more of the aforementioned carriers, is advantageously brought into a suitable dosage unit form. The dose chosen should comply with the activity of the benzenesulfonyl-urea used and with the desired effect. Advantageously, the dosage per unit amounts to about 0.5 to 100 mg, preferably 2 to 10 mg, but considerably higher or lower dosage units may also be used, which, where required are divided or multiplied prior to their administration.

The following Examples serve to illustrate some variants of the process, which may be used for the synthesis of the benzenesulfonyl-ureas of the invention.

EXAMPLE 1

N-[4-($\beta$-<2-methoxy-5-chlorobenzamido>-ethyl)-benzenesulfonyl]-N'-cyclopentyl-urea 2.45 g of N-[4-($\beta$-<2-methoxy-5-chlorobenzamido>-ethyl)-benzenesulfonyl]-phenylurethane (obtained from 4-[$\beta$-(2-methoxy-5-chlorobenzamido)-ethyl]-benzenesulfonamide and chloroformic acid phenyl ester) were refluxed for 2 hours with 0.43 g of cyclopentyl-amine in 30 ml of dioxane. After dilution with water and acidification with dilute hydrochloric acid a precipitate was obtained which was treated with 0.5 %-ammonia. The aqueous alkaline solution was acidified and the precipitate obtained was recrystallized from methanol. N-[4-($\beta$-<2-methoxy-5-chlorobenzamido>-ethyl)-benzenesulfonyl]-N'-cyclopentyl-urea, melting point 184°– 185°C, was obtained.

EXAMPLE 2

N-[4-($\beta$-<2-methoxy-5-chlorobenzamido>-ethyl)-benzenesulfonyl]-N'-cyclopentyl-urea 4.26 g of N-[4-($\beta$-<2-methoxy-5-chloro-benzamido>-ethyl)-benzenesulfonyl]-methylurethane were heated for one and a half hour with 1.5 g of cyclopentyl-amine acetate in 100 ml of dioxane, using a descending condenser.

After addition of water and recrystallization of the product obtained from methanol N-[4-($\beta$-<2-methoxy-5-chlorobenzamido>-ethyl)-benzenesulfonyl]-N'-cyclopentyl-urea, melting point 184° – 185°C, was obtained in a very good yield.

EXAMPLE 3

N-[4-($\beta$-<2-methoxy-5-chloro-benzamido>-ethyl)-benzenesulfonyl]-N'-cyclopentyl-urea A mixture of 10.3 g of N-[4-($\beta$-<2-methoxy-5-chlorobenzamido>-ethyl)-benzenesulfonyl]-urea (m.p. 171° – 173°C), 300 ml of toluene, 30 ml of glycolmonomethyl ether, 1.65 g of glacial acetic acid and 2.4 g of cyclopentyl-amine was refluxed for 5 hours. Subsequently, the mixture was concentrated in vacuo and the residue was treated with alcohol. N-[4-($\beta$-<2-methoxy-5-chlorobenzamido>-ethyl)-benzenesulfonyl]-N'-cyclopentyl-urea obtained as a raw product was separated by suction-filtration and recrystallized from methanol. Melting point 184° – 185°C.

EXAMPLE 4

N-[4-($\beta$-<2-methoxy-5-chlorobenzamido>-ethyl)-benzenesulfonyl]-N'-cyclopentyl-urea 4.9 g of N-[4-($\beta$-<2-methoxy-5-chlorobenzamido>-ethyl)-benzenesulfonyl]-N'-phenyl-urea (m.p. 193° – 195°C), 100 ml of dioxane and 0.85 g of cyclopentyl-amine were refluxed for 1 hour.

The clear solution was subsequently concentrated in vacuo and the residue obtained was treated with about 0.5 %-ammonia. After clarification of the solution by filtration it was acidified. The precipitate of N-[4-($\beta$-<2-methoxy-5-chloro-benzamido>-ethyl)-benzenesulfonyl]-N'-cyclopentyl-urea obtained was isolated by suction-filtration and dried. After recrystallization from methanol a product was obtained having the melting point of 184° – 185°C.

EXAMPLE 5

N-[4-($\beta$-<2-methoxy-5-chloro-benzamido>-ethyl)-benzenesulfonyl]-N'-cyclopentyl-urea 2.3 g of N-[4-($\beta$-<2-methoxy-5-chlorobenzamido>-ethyl)-benzenesulfonyl]-N'-acetyl-urea (m.p. 208°C with decomposition) and 0.43 g of cyclopentyl-amine were carefully mixed. Upon heating, the cyclopentyl-amine salt of N-[4-($\beta$-<2-methoxy-5-chlorobenzamido>-ethyl)-benzenesulfonyl]-N'-acetyl-urea was formed. The salt was heated in an Erlenmeyer flask for 45 minutes to 150°C in an oil bath. After several minutes the salt melted to form a clear melt.

The melt was cooled, treated with aqueous 0.5 %-ammonia while heating on the steam bath, then filtered and the filtrate was acidified. The precipitated crystals were separated by suction-filtration and taken up once more in 0.5 %-ammonia.

Upon acidification of the filtrate, a crystalline precipitate of N-[4-($\beta$-<2-methoxy-5-chlorobenzamido>-ethyl)-benzenesulfonyl]-N'-cyclopentyl-urea was obtained, separated by suction-filtration and dried. After recrystallization from methanol the substance was found to melt at 183° – 184°C.

EXAMPLE 6

N-[4-($\beta$-<2-methoxy-5-chloro-benzamido>-ethyl)-benzenesulfonyl]-N'-cyclopentyl-urea 6.5 g of sodium salt of 4-($\beta$-<2-methoxy-5-chlorobenzamido>-ethyl)-benzenesulfonamide were refluxed for 3 hours with 3.9 g of diphenylcarbamic acid chloride in 60 ml of toluene. The crude N-[4-($\beta$-<2-methoxy-5-chlorobenzamido>-ethyl)-benzenesulfonyl]-N',N'-diphenyl-urea obtained was suction-filtered, suspended in dioxane and, after addition of 1 g of acetic acid and 1.6 g of cyclopentyl-amine, the substance was refluxed for 1½ hours. After acidification with dilute hydrochloric acid the precipitate was separated by suction-filtration and treated with 0.5 %-ammonia. The aqueous alkaline solution was acidified and the crystals were re-crystallized from methanol. N-[4-($\beta$-<2-methoxy-5-chloro-benzamido>-ethyl)-benzenesulfonyl]-N'-cyclopentyl-urea was obtained having a melting point of 182° – 184°C.

EXAMPLE 7

N-[4-(β-<2-methoxy-5-chlorobenzamido>-ethyl)-benzenesulfonyl]-N'-cyclopentyl-urea 0.95 g of N,N'-bis-[4-(β-<2-methoxy-5-chlorobenzamido<-ethyl)-benzenesulfonyl]-urea (m.p. 183° – 185°C) were suspended in 30 ml of dioxane. 0.107 g of cyclopentyl-amine were added and the whole was refluxed for 1 hour. After concentration of the clear solution obtained the residue was treated with 0.5 %-aqueous ammonia, the 4-(β-<2-methoxy-5-chlorobenzamido>-ethyl)-benzenesulfonamide formed was separated by filtration and acidified. A crystalline precipitate of N-[4-(β-<2-methoxy-5-chlorobenzamido>-ethyl)-benzenesulfonyl]-N'-cyclopentyl-urea was obtained, isolated by suction-filtration, dried and recrystallized from methanol. Melting point 182° – 184°C.

EXAMPLE 8

N-[4-(β-<2-methoxy-5-chlorobenzamido>-ethyl)-benzenesulfonyl]-N'-cyclopentyl-urea 4.95 g of 4-[4-(β-<2-methoxy-5-chloro-benzamido>-ethyl)-benzenesulfonyl]-1,1-pentamethylene-semicarbazide, melting point 165° – 167°C, 50 ml of dioxane and 0.85 g of cyclopentyl-amine were refluxed for 45 minutes. The solution obtained was concentrated in vacuo and the residue was taken up in about 0.5 %-aqueous ammonia. The solution was filtered and the filtrate was acidified. A crystalline precipitate of N-[4-(β-<2-methoxy-5-chlorobenzamido>-ethyl)-benzenesulfonyl]-N'-cyclopentyl-urea was obtained, separated by suction filtration and dried. After recrystallization from methanol the substance was found to melt at 183° – 185°C.

EXAMPLE 9

N-[4-(β-<2-methoxy-5-chlorobenzamido>-ethyl)-benzenesulfonyl]-N'-cyclopentyl-urea 1.8 g of 4-[4-(β-<2-methoxy-5-chloro-benzamido>-ethyl)-benzenesulfonyl]-cyclooctanone-semicarbazone, 50 ml of dioxane and 0.29 g of cyclopentyl-amine were refluxed for 1 hour. The clear solution was concentrated in vacuo and the residue obtained was treated with about 0.5 %-aqueous ammonia. After filtration the filtrate was acidified. A crystalline precipitate of N-[4-(β-<2-methoxy-5-chlorobenzamido>-ethyl)-benzenesulfonyl]-N'-cyclopentyl-urea was obtained, separated by suction-filtration, dried and recrystallized from methanol. The melting point of the substance was 182° – 184°C.

EXAMPLE 10

N-[4-(β-<2-methoxy-5-chlorobenzamido>-ethyl)-benzenesulfonyl]-N'-cyclopentyl-urea 7.5 g of 4-(β-<2-methoxy-5-chlorobenzamido>-ethyl)-benzene-sulfonamide and 5.6 g. of ground potassium carbonate were suspended in 150 ml of acetone and refluxed for 3 hours. Subsequently, 2.3 g of cyclopentyl-isocyanate (prepared by reaction of cyclopentylamine-hydrochloride with phosgene, boiling point 55°C under a pressure of 35 mm mercury) were added thereto and the whole was heated for another 5 hours. The precipitate formed was separated by suction-filtration, suspended in water and acidified with dilute hydrochloric acid. After suction-filtration, N-[4-(β-<2-methoxy-5-chlorobenzamido>-ethyl)-benzene-sulfonyl]-N'-cyclopentyl-urea was obtained which after recrystallization from methanol was found to melt at 184° – 185°C.

EXAMPLE 11

N-[4-(β-<2-methoxy-5-chlorobenzamido>-ethyl)-benzenesulfonyl]-N'-cyclopentyl-urea 3.9 g of sodium salt of 4-(β-<2-methoxy-5-chlorobenzamido>-ethyl)-benzenesulfonamide and 4.1 g of N-cyclopentyl-carbamic acid phenyl ester (prepared from chloroformic acid phenyl ester and cyclopentyl-amine) were dissolved in 100 ml of dimethylformamide. The solution was heated to 110°C for 45 minutes, then allowed to cool and poured in about 0.5 %-aqueous ammonia. The undissolved substance was separated by filtration and the filtrate was acidified. The crystallized precipitate of N-[4-(β-<2-methoxy-5-chlorobenzamido>-ethyl)-benzenesulfonyl]-N'-cyclopentyl-urea which had precipitated was separated by suction-filtration, washed and dried. After recrystallization from methanol the substance was found to melt at 182° – 184°C.

EXAMPLE 12

N-[4-(β-<2-methoxy-5-chlorobenzamido>-ethyl)-benzenesulfonyl]-N'-cyclopentyl-urea 3.9 g of sodium salt of 4-(β-<2-methoxy-5-chlorobenzamido>-ethyl)-benzenesulfonamide and 3.84 g of cyclopentyl-urea (m.p. 196° – 197°C) were well mixed in a mortar and heated to 200°C for 10 minutes in an Erlenmeyer flask on a pre-heated oil bath. After cooling, the melt was heated with about 0.5 %-ammonia on a steam bath. The solution was filtered and the filtrate was acidified. The precipitate obtained was suction-filtered and taken up once more in 0.5 %-ammonia. After another acidification of the filtrate the precipitate obtained was isolated by suction-filtration, dried and re-crystallized from methanol.

The N-[4-(β-<2-methoxy-5-chlorobenzamido>-ethyl)-benzenesulfonyl]-N'-cyclopentyl-urea obtained was found to melt at 182° – 184°C.

EXAMPLE 13

N-[4-(β-<2-methoxy-5-chlorobenzamido>-ethyl-benzenesulfonyl]-N'-cyclopentyl-urea 3.9 g of sodium salt of 4-(β-<2-methoxy-5-chlorobenzamido>-ethyl)-benzene-sulfonamide and 3.4 g of N-acetyl-N'-cyclopentyl-urea (m.p. 97° – 98°C, prepared from cyclopentyl-urea and acetoanhydride) were heated to 110°C for 2 hours in 100 ml of dimethylformamide. The solution obtained was concentrated under reduced pressure to two-thirds of its volume and then water and hydrochloric acid were added thereto. The solution was suction-filtered and the residue was treated with 0.5 %-aqueous ammonia. After filtration the filtrate was acidified and the precipitate obtained was isolated by suction-filtration, washed and dried. After recrystallization from methanol, N-[4-(β-<2-methoxy-5-chlorobenzamido>-ethyl)-benzenesulfonyl]-N'-cyclopentyl-urea was obtained having a melting point of 183° – 185°C.

EXAMPLE 14

N-[4-(β-<2-methoxy-5-chloro-benzamido>-ethyl)-benzenesulfonyl]-N'-cyclopentyl-urea 3.9 g of sodium salt of 4-(β-<2-methoxy-5-chlorobenzamido>-ethyl)-benzenesulfonamide; 5.6 g of N,N-diphenyl-N'-cyclopentyl-urea (m.p. 137° – 138°C, prepared from diphenyl carbamic acid chloride and cyclopentyl-amine) and 100 ml of dimethylformamide were heated to 110°C for 45 minutes. (After several minutes a clear solution had formed). The solution was cooled, poured into water and then 0.5 %-ammonia was added thereto. After filtration the filtrate was acidified, the precipitate obtained was separated by suction-filtration and introduced once more into 0.5 %-ammonia. After filtration and acidification of the filtrate a crystalline precipitate of N-[4-(β-<2-methoxy-5-chlorobenzamido>-ethyl)-benzene-sulfonyl]-N'-cyclopentyl-urea was obtained which, after drying and recrystallization from methanol, was found to melt at 183° – 185°C.

EXAMPLE 15

N-[4-(β-<2-methoxy-5-chlorobenzamido>-ethyl)-benzenesulfonyl]-N'-cyclopentyl-urea 2 g of sodium salt of 4-(β-<2-methoxy-5-chlorobenzamido>-ethyl)-benzenesulfonamide and 2.2 g of N,N'-dicyclopentyl-urea (m.p. 248° – 249°C, prepared from cyclopentyl-isocyanate and cyclopentyl-amine) were well mixed in a mortar. The mixture was heated to 220°C for 10 minutes in an Erlenmeyer flask on a preheated oil bath. After cooling, the sintered reaction cake was treated with 0.5 %-ammonia. After filtration, the filtrate was acidified and a precipitate was obtained which was separated by suction-filtration and dissolved once more in 0.5 %-ammonia. After filtration, the filtrate was acidified. The precipitate of crude N-[4-(β-<2-methoxy-5-chlorobenzamide>-ethyl)-benzenesulfonyl]-N'-cyclopentyl-urea that had separated was isolated by suction-filtration and dried. By treatment with methanol an at first smeary and then crystalline substance was obtained, which after suction-filtration, was once more recrystallized from methanol. The melting point of N-[4-(β-<2-methoxy-5-chloro-benzamido>-ethyl)-benzenesulfonyl]-N'-cyclopentyl-urea obtained was 182° – 184°C.

EXAMPLE 16

N-[4-(β-<2-methoxy-5-chlorobenzamido>-ethyl)-benzenesulfonyl]-N'-cyclopentyl-urea a. Potassium salt of N-[4-(β-<2-methoxy-5-chlorobenzamido>-ethyl)-benzenesulfonyl]-iminodithio-carbonic acid.

74 g of 4-(β-<2-methoxy-5-chlorobenzamido>-ethyl)-benzenesulfonamide were dissolved in 350 ml of dimethylformamide. 23 g of carbon disulfide and subsequently a solution of 34 g of potassium hydroxide in 50 ml of water were added thereto dropwise, while stirring. Stirring was continued for 3 hours at room temperature and the clear solution obtained was poured into 4 l of ethanol. The potassium salt of N-[4-(β-<2-methoxy-5-chlor-benzamido>-ethyl)-benzenesulfonyl]-iminodithio-carbonic acid which had precipitated was isolated by suction-filtration, washed with alcohol and dried. Yield 60 g.

b.
N-[4-(β-<2-methoxy-5-chloro-benzamido>-ethyl)-benzenesulfonyl]-iminodithio-carbonic acid dimethyl ester.

36 g of the potassium salt obtained according to (a) were dissolved in 60 ml of 1-normal sodium hydroxide solution. While shaking, 12.6 g of dimethyl sulfate were added to the clear solution, whereupon the temperature of the solution rose. After standing for 30 minutes, the solution was decanted to separate a semisolid smeary precipitate. After washing with water, the smeary precipitate crystallized. The crystalline substance was recrystallized from dilute methanol, whereby 30 g of N-[4-(β-<2-methoxy-5-chlorobenzamido>-ethyl-benzenesulfonyl]-iminodithio-carbonic acid dimethyl ester, which was found to melt at 94° – 96°C, were obtained.

c.
N-[4-(β-<2-methoxy-5-chlorobenzamido>-ethyl)-benzenesulfonyl]-N'-cyclopentyl-isothio-urea methyl ether.

4.73 g of the ester obtained according to b) were dissolved in 100 ml of dioxane. 0.85 g of cyclopentyl-amine was added thereto and the whole was heated on the steam bath for 1½ hours. After pouring into water and acidification with hydrochloric acid, the isothio-urea-methyl ether indicated above was obtained as a smeary substance.

d.
N-[4-(β-<2-methoxy-5-chlorobenzamido>-ethyl)-benzenesulfonyl]-N'-cyclopentyl-urea.

The smeary substance obtained according to (c) was dissolved in dioxane, a 2-normal sodium hydroxide solution was added thereto and the solution was heated for 1 hour on the steam bath. After pouring into water and acidification with acetic acid, N-[4-(β-<2-methoxy-5-chlorobenzamido>-ethyl)-benzenesulfonyl]-N'-cyclopentyl-urea was obtained as a crystallized precipitate. The substance was found to melt, after recrystallization from methanol, at 183° – 185°C.

EXAMPLE 17

N-[4-(β-<2-methoxy-5-chlorobenzamido>-ethyl)-benzenesulfonyl]-N'-cyclopentyl-urea a. 4.9 g of cyclopentyl-parabanic acid (m.p. 111° – 112°C) and 2.5 g of triethylamine were dissolved in 200 ml of benzene and 8.9 g of 4-(β-<2-methoxy-5-chlorobenzamido>-ethyl)-benzenesulfochloride (m.p. 102° – 103°C) were added thereto. The mixture was refluxed for 3 hours and the triethylamine hydrochloride formed was separated while hot by suction-filtration. Petroleum ether was added to the cooled filtrate and the crystals which precipitated after a short time were separated by suction-filtration. After the crystals had been recrystallized two times from a mixture of methanol and dimethylformamide, the pure 1-[4-(β-<2-methoxy-5-chlorobenzamido>-ethyl)-benzenesulfonyl]-3-cyclopentyl-parabanic acid, melting point 181° – 183°C, was obtained.

b. 0.5 g of the substance obtained according to a) was heated with 5 ml of dioxane and 10 ml of 1-normal sodium hydroxide solution for 45 minutes on the steam bath. Water was then added thereto, the mixture was acidified and the precipitate obtained was recrystallized from methanol. The melting point of the N-[4-(β-<2-methoxy-5-chlorobenzamido>-ethyl)-benzenesulfonyl]-N'-cyclopentyl-urea so obtained was 183° – 185°C.

EXAMPLE 18

N-[4-(β-<2-methoxy-5-chlorobenzamido>-ethyl)-benzensulfonyl]-N'-cyclopentyl-urea a. 3 g of N-[4-(β-<2-methoxy-5-chlorobenzamido>-ethyl)-benzenesulfonyl]-N'-cyclopentyl-thiourea (prepared from N-[4-(β-<2-methoxy-5-chlorobenzamido>-ethyl)-benzenesulfonyl]-N'-phenyl-urea and cyclopentyl-amine, m.p. 150° – 152°C) were suspended in 50 ml of 2-normal sodium hydroxide solution. Subsequently 10 ml of 35 %-hydrogen peroxide were added thereto and the whole was heated for 30 minutes on the steam bath, acidified with dilute hydrochloric acid, the crystalline precipitate was separated by suction-filtration and recrystallized from methanol. The isolated N-[4-(β-<2-methoxy-5-chlorobenzamido>-ethyl)-benzenesulfonyl]-N'-cyclopentyl-urea was found to melt, after recrystallization from methanol, at 183° – 185°C.

The same compound was obtained when the thiourea mentioned above was desulfurized by treating it with mercury-(II) oxide in the presence of a sodium hydroxide solution. For this purpose 0.5 g of the thiourea was dissolved in 10 ml of dioxane and 10 ml of a 2-normal sodium hydroxide solution. 0.22 g. of mercury oxide was added thereto and the whole was stirred for 4 hours at 40°C. The mercury-(II) sulfide, which had formed, was removed by suction filtration, the filtrate was acidified and the precipitate of N-[4-(β-<2-methoxy-5-chlorobenzamido>-ethyl)-benzenesulfonyl]-N'-cyclopentyl-urea obtained was separated by suction-filtration and recrystallized from methanol. Melting point 183° – 185°C.

b. 0.5 g of N-[4-(β-<2-methoxy-5-chlorobenzamido>-ethyl)-benzenesulfonyl]-N'-cyclopentyl-thiourea was dissolved in 50 ml of methanol. 0.22 g of mercury-(II) oxide and a small amount of $K_2CO_3$ were added thereto while stirring and the whole was heated to 50° – 55°C for 3 hours while stirring was continued. After removal by filtration of the mercury-(II) sulfide formed, the solution was concentrated whereupon the N-[4-(β-<2-methoxy-5-chlorobenzamido>-ethyl)-benzenesulfonyl]-N'-cyclopentyl-isourea methyl ether was obtained as a viscous resin. A sample of the above-mentioned isourea ether was covered with concentrated hydrochloric acid in a test tube and, while stirring, heated for several minutes on the steam bath. The crystalline product, constituting N-[4-(β-<2-methoxy-5-chlorobenzamido>-ethyl)-benzenesulfonyl]-N'-cyclopentyl-urea was recrystallized from methanol. M.p. 181° – 183°C.

EXAMPLE 19

N-[4-(β-<2-methoxy-5-chlorobenzamido>-ethyl)-benzenesulfonyl]-N'-cyclopentyl-urea 3.1 g of N-[4-(β-aminoethyl)-benzenesulfonyl]-N'-cyclopentyl-urea (prepared by saponification of N-[4-(β-acetaminoethyl)-benzenesulfonyl]-N'-cyclopentyl-urea with sodium hydroxide solution) were suspended in 25 ml of chloroform. After addition of 1.6 g of pyridine, 2.1 g of 2-methoxy-5-chlorobenzoic acid chloride were introduced and, while stirring, the whole was heated to 40°C for 6 hours. The solution that had formed was concentrated in vacuo and the smeary residue was extracted with 1 %-ammonia. After acidification of the alkaline solution and recrystallization from methanol, N-[4-(β-<2-methoxy-5-chlorobenzamido>-ethyl)-benzenesulfonyl]-N'-cyclopentyl-urea, melting point 183° – 185°C, was obtained.

We claim:

1. Process for the lowering of the blood sugar level in a diabetic patient which comprises administering to the patient an effective amount for lowering blood sugar of N-[4-(β-<2-methoxy-5-chlorobenzamido>-ethyl)-benzenesulfonyl]-N'-cyclopentyl-urea of the formula

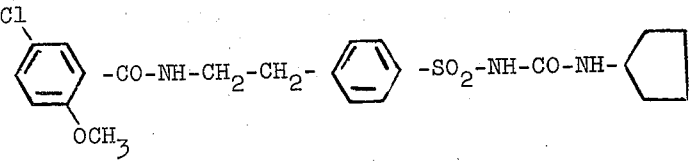

and a salt thereof of a pharmaceutically acceptable base.

2. Pharmaceutical preparation having hypoglycemic activity which comprises an effective amount for lowering blood sugar level of the compound identified in claim 1 and a pharmaceutically suitable carrier therefore.

* * * * *

UNITED STATES PATENT AND TRADEMARK OFFICE
CERTIFICATE OF CORRECTION

PATENT NO. : 3,932,658
DATED : January 13, 1976
INVENTOR(S) : Helmut Weber, Walter Aumuller, Karl Muth and Rudi Weyer It is certified that error appears in the above-identified patent and that said Letters Patent are hereby corrected as shown below:

In the Heading between Items [62] and [52], insert:

-- [30] Foreign Application Priority Data

February 25, 1969    Germany    P 19 09 272 --

Signed and Sealed this sixth Day of April 1976

[SEAL]

Attest:

RUTH C. MASON
*Attesting Officer*

C. MARSHALL DANN
*Commissioner of Patents and Trademarks*